US008726564B2

(12) United States Patent
Lagunas-Solar et al.

(10) Patent No.: US 8,726,564 B2
(45) Date of Patent: May 20, 2014

(54) DISINFESTATION AND DISINFECTION OF FOOD, PERISHABLES AND OTHER COMMODITIES

(75) Inventors: Manuel C. Lagunas-Solar, Davis, CA (US); Timothy K. Essert, Sacramento, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/179,855

(22) Filed: Jul. 11, 2011

(65) Prior Publication Data

US 2012/0005948 A1 Jan. 12, 2012

Related U.S. Application Data

(63) Continuation of application No. 11/429,647, filed on May 5, 2006, now Pat. No. 7,975,427, which is a continuation of application No. PCT/US2004/013225, filed on Apr. 3, 2004.

(60) Provisional application No. 60/517,806, filed on Nov. 5, 2003.

(51) Int. Cl.

| | |
|---|---|
| ***A01M 1/20*** | (2006.01) |
| ***A01M 5/00*** | (2006.01) |
| ***A01M 7/00*** | (2006.01) |
| ***A01M 17/00*** | (2006.01) |

(52) U.S. Cl.
USPC .......... 43/132.1

(58) Field of Classification Search
USPC .......... 43/58, 124, 125, 132.1, 107, 112
See application file for complete search history.

(56) References Cited

U.S. PATENT DOCUMENTS

| | | | | |
|---|---|---|---|---|
| 2,257,541 | A | | 9/1941 | Smith |
| 4,366,644 | A | | 1/1983 | Lawrence |
| 4,782,623 | A | | 11/1988 | Lawrence |
| 4,958,456 | A | | 9/1990 | Chaudoin et al. |
| 4,966,755 | A | | 10/1990 | Smith |
| 4,989,363 | A | * | 2/1991 | Doernemann .......... 43/124 |
| 5,162,052 | A | | 11/1992 | Hoffmann et al. |
| 5,365,691 | A | | 11/1994 | Scherkenbeck et al. |
| 5,365,692 | A | * | 11/1994 | Gustafson .......... 43/124 |
| 5,403,597 | A | | 4/1995 | Mueller |
| 5,458,901 | A | * | 10/1995 | Engler et al. .......... 426/521 |

(Continued)

OTHER PUBLICATIONS

ISA/US, international search report and written opinion issued on Oct. 29, 2004, related PCT Application No. PCT/US2004/013225, including application and claims searched, pp. 1-85.

(Continued)

*Primary Examiner* — Joshua Michener
(74) *Attorney, Agent, or Firm* — John P. O'Banion

(57) ABSTRACT

A method and system for disinfecting and disinfesting a commodity, such as a perishable agricultural commodity, by treatment with an environment of low oxygen/high ballast gas with cycled pressure changes that overwhelm and damage the respiratory system of the insect without damaging the host commodity. The system and method may also include the introduction of disinfectants, antiseptics and other toxic chemicals or the exposure to radio frequencies with intense electric fields that may increase the metabolic activity of the pest or decrease the fitness of the pest within the low oxygen environment. Treatments according to the methods can also increase the shelf life of agricultural commodities by eradicating or delaying the growth of bacteria, fungi, protozoa and other microbial pests.

22 Claims, 2 Drawing Sheets

(56) References Cited

U.S. PATENT DOCUMENTS

| | | | |
|---|---|---|---|
| 5,520,881 | A | 5/1996 | Koestler et al. |
| 5,968,401 | A | 10/1999 | Roy |
| 6,171,561 | B1 | 1/2001 | Williamson et al. |
| 6,537,601 | B1 * | 3/2003 | Voisin .......................... 426/113 |
| 6,615,534 | B1 | 9/2003 | Smithyman et al. |
| 6,766,612 | B1 | 7/2004 | Liu |
| 6,837,001 | B2 | 1/2005 | Amburgey et al. |
| 7,975,427 | B2 * | 7/2011 | Lagunas-Solar et al. .... 43/132.1 |
| 2002/0182104 | A1 | 12/2002 | Carman et al. |
| 2003/0014907 | A1 | 1/2003 | Amburgey et al. |
| 2004/0033296 | A1 * | 2/2004 | Yuan et al. .................... 426/326 |
| 2005/0246942 | A1 | 11/2005 | Mueller et al. |
| 2006/0179708 | A1 | 8/2006 | Garland |
| 2007/0068067 | A1 | 3/2007 | Ragon et al. |
| 2008/0255498 | A1 * | 10/2008 | Houle ............................. 604/20 |
| 2008/0307694 | A1 | 12/2008 | Nichols |
| 2012/0291458 | A1 * | 11/2012 | Seibert et al. ..................... 62/78 |

OTHER PUBLICATIONS

USPTO, Non-final Office Action Issued on Sep. 5, 2012, Including Claims, for U.S. Appl. No. 13/179,838, pp. 1-30.

* cited by examiner

DISINFESTATION AND DISINFECTION OF FOOD, PERISHABLES AND OTHER COMMODITIES

CROSS-REFERENCE TO RELATED APPLICATIONS

This application is a continuation of U.S. patent application Ser. No. 11/429,647 filed on May 5, 2006, now U.S. Pat. No. 7,975,427, incorporated herein by reference in its entirety, which is a continuation of PCT international application serial number PCT/US2004/013225, filed on Apr. 30, 2004, incorporated herein by reference in its entirety, which claims priority from U.S. Provisional Patent Application Ser. No. 60/517,806 filed on Nov. 5, 2003, incorporated herein by reference in its entirety. Priority is claimed to each of the foregoing applications.

The above-referenced PCT international application was published on May 26, 2005 as PCT International Publication No. WO 2005/046743, incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to insect and other pest control treatments and more particularly to methods for rapidly eliminating infestations of insects and other living organisms from commodities using low oxygen atmospheres, pressure differentials and metabolism manipulations with disinfectants, antiseptics, toxics or exposure to intense non-thermal radio frequencies.

2. Description of the Related Art

Every year considerable quantities of pesticides are applied to commodities by producers at various stages of agricultural production, from pre-planting to post harvest, in order to eradicate unwanted insects and other animal, microbial and fungal pests. The presence of egg, larval and adult forms of insects creates the possibility of cross-infestation of commodities and increasing losses during transportation and storage. Established quarantine barriers regulate transportation of agricultural commodities worldwide in order to reduce the potential for propagation and transportation of non-indigenous pests. Many commodities cannot be legally imported or exported to various countries without pesticide treatments to eliminate quarantine pests and to certify that the commodities are free from pests.

Methyl bromide, for example is widely used in the industry as a gaseous fumigant that can disinfest a variety of fresh foods, agricultural soils and structural facilities. However, methyl bromide is scheduled to be banned in the next few years because of the capability of methyl bromide to scavenge ozone in the atmosphere. Agriculture in the United States used about 60 million pounds of methyl bromide before the mandatory reductions began in 1999.

The use of methyl bromide or other chemicals in the fresh fruit industry is often unsatisfactory due to the creation of cosmetic blemishes or a reduction in the effective shelf life of the fruit. In addition, applications of methyl bromide at concentrations sufficient to control pests on stored and exported commodities may produce bromide residue levels that are relatively high.

Likewise, other pesticides known in the art have shown erratic performance at low concentrations and have produced crop damage and unacceptable residue levels in some cases. Other pesticides that are widely used with pre-harvest and post-harvest applications include phosphine, chloropicrin, 1,3-dichloropropene, Telone/Vapam, sulfaryl fluoride and hydrogen cyanide. The use of pesticides in general and these insecticides in particular are of global concern due to the detrimental effects they have on animals, air, water and soil as well as the impact they have on public health and agricultural workers.

Another approach to the eradication of insect infestation in food commodities in the art is the use of thermal energy. However, thermal energy, such as the use of hot water, is unsatisfactory because it can cause rapid deterioration of the commodity and typically uses a large amount of energy. Thermal energy is normally used in the fresh produce industry only when no other alternatives are viable or available.

A further approach to disinfestation has been to expose the commodity to a controlled atmosphere with low oxygen concentrations and increased carbon dioxide concentrations. However, these techniques have been inconsistent and often ineffective for eliminating insects, mites and other pests. Present controlled atmosphere approaches require several days to weeks to conduct and are therefore of limited use in the fresh produce industry. One reason that controlled atmosphere techniques are only marginally effective is that many insects can survive low oxygen or increased carbon dioxide environments by collapsing portions of their respiratory system to form air sacks providing a reserve of oxygen. Such reserves may allow some types of insects to survive for several days or more.

Furthermore, some fresh foods may experience detrimental changes in color, texture, acidity and other characteristics from prolonged exposure to high carbon dioxide environments. Accordingly, controlled atmosphere techniques are not considered viable for disinfestation and quarantine applications with fresh produce.

Additionally, there are major human safety concerns that exist today from the potential contamination of food commodities with pathogenic bacteria such as *Escherichia coli* O157:H7, *Salmonella* sp., *Listeria*, and especially *Campylobacter*. Each of these pathogenic bacteria has recently been identified as disease causing agents from the consumption of many common food commodities. It is estimated that outbreaks of food borne illnesses in the United States affect 12 million people and result in the death of approximately 4,000 individuals annually. Similarly, the control of protozoa (i.e. *Toxoplasma* sp., *Cryptosporidium* sp., and/or *Cyclospora* sp.) and other parasites on many foods and especially on fresh fruits and vegetables is an important challenge for agricultural producers. For example, humans may become infected with parasites by ingesting tissue cysts from undercooked meat or other infected food or water. Recently, several outbreaks of *Cyclospora* associated gastroenteritis in humans were linked to the consumption of raspberries, lettuce and basil. There are presently no practical methods available to disinfect foods from infective oocysts.

Microbial activity may also generate a variety of toxins, such as Aflatoxin from *Aspergillius flavus* in grains, that are detrimental to public health or may otherwise make the commodity lose its value in the marketplace. Agricultural commodities such as fresh produce, grains, seeds, and spices may also be affected by fungal and/or bacterial contaminants. It is therefore desirable to inhibit the presence of disease-carrying organisms within food and agricultural commodities as well as eradicate insect infestations. This can be accomplished by either slowing down the development of spoilage organisms (biostatic effects) or by casing a lethal effect on the organism (biocidal effect).

Accordingly, there is a need for an apparatus and method for eradicating a wide variety of insect and microbial pests that is effective and does not leave toxic residues or alter the characteristics of the commodity that is treated. The present invention satisfies these needs as well as others and generally overcomes the deficiencies in the art.

BRIEF SUMMARY OF THE INVENTION

The present invention generally provides a method for rapid, quarantine level disinfestation of insects, mites and other biological pests from a variety of commodities such as fresh, dried or processed foods as well as cut flowers, soils and historical artifacts and the like. The method may also provide biostatic effects (i.e. delays of microbial growth) or biocidal effects on microbes such as protozoa, bacteria and fungi that are often responsible for reducing the shelf life or storage life of a commodity.

The method is based on sequestering the food commodity for a period of time, typically less than 24 hours and often 1 to 6 hours, in a container preferably containing an environment with extremely low oxygen (preferably less than 0.01%) and a high carbon dioxide (preferably greater than 99.9%) levels, at above or below barometric pressure. The method includes an initial pressure cycling procedure that is designed to manipulate the respiratory system of the insects in order to overcome their ability to establish a reserve of air within collapsible air sacs. The mechanical forces applied to the respiratory system of the pests by the cyclic pressure differential may also damage the tubular respiratory network. Such damage reduces the overall capacity of the respiratory system to exchange gases as well as to increase the sensitivity of the insect pest to low oxygen or high carbon dioxide conditions. The duration of treatment, the number of cyclic repetitions and the size of the pressure differential can be adapted to the sensitivity of the insect pest and the commodity to anoxic environments. In this manner, mortality effects are maximized and pest survival is greatly reduced over time allowing the procedure to be completed in the range of less than 1 hour to 24 hours.

The gaseous environment used for disinfestation may also induce simultaneous microbial eradication or growth delay effects for 2-3 days and longer at room temperature. The growth delay effects can be extended effectively to 8-10 days or more under refrigerated storage. Due to the short time required for effective disinfestation and the non-toxic nature of the gases involved, the potential for sensory and/or physiological changes in the host commodity (i.e. due to anaerobic respiration or fermentation) are largely avoided. In addition, the shortened time makes the method a practical and economical approach over previous attempts to use modified atmospheres for disinfestation and disinfection of foods and fresh horticultural perishable commodities.

In one embodiment, a method is provided that includes sequestering a host commodity to be treated in a container or enclosure for a period of time less than approximately 24 hours. An environment is created in the container that preferably contains less than approximately 0.01%) oxygen and approximately 99.9% ballast gas or gases (i.e. carbon dioxide, nitrogen, others). Although very low oxygen conditions are preferred, higher levels of oxygen can be used. The environment is maintained at above or below barometric pressure. In one embodiment, the enclosure is configured to permit the interior to be maintained at below the ambient barometric pressure. In another, the environment is maintained at levels above the ambient barometric pressure. A further embodiment provides a container that can expose a commodity to atmospheres that cycle from below to above or from above to below ambient barometric pressures etc. for one or more cycles.

The initial cycling of positive and negative pressures designed to manipulate the insect's respiratory system may also be repeated periodically in order to vent any detrimental gases formed from metabolic processes in fruits and vegetables so as to avoid or minimize the potential for physiological changes including anaerobic fermentation when overall treatment times extend to several hours.

The use of carbon dioxide or nitrogen as a ballast gas at normal or slightly greater barometric pressures may also induce changes in the cellular metabolism of the insects, mites or microbial contaminants. For example, the use of carbon dioxide can change the acid-base equilibrium or displace the oxygen equilibrium within the respiratory system and body of the insect pest.

In order to accelerate mortality and other biological effects on insects and microbes, additional metabolic stress may be applied to the pests. In one embodiment, further metabolic stress may be generated through the use of an oscillating radio frequency field with appropriate electric field intensities. The interaction of RF generated electric fields with insects and mites cause increased oxygen demands because the conductive insects attempt to physically align themselves to rapidly changing field orientations. The radio frequency fields may also have a direct effect on the fitness of the insects and other pests by weakening and damaging the insects and reducing their tolerance of the anoxic environment.

In another embodiment, metabolically toxic disinfectants like ozone or hydrogen peroxide and/or antiseptics such as ethanol may be quickly evaporated within the container or added externally into a reduced pressure environment to allow for their rapid gasification and a complete distribution over the commodity's surface. The use of such disinfectants not only assists with disinfestation, it has the added benefit of providing disinfection of the commodity as well.

Alternatively, in another embodiment, oxygen radicals and ozone can be produced in situ within the commodity container using oscillating or pulsed radio frequency fields. Ozone and oxygen radicals may also be introduced from an external source. Oxygen radicals and ozone in small quantities induce toxic effects to cellular metabolism as well as metabolic stress to an insect pest.

In another embodiment, the environment in the container includes toxic gases or regulated pesticides in addition to the low oxygen and high ballast gas environment. Gases or vapors that are toxic to insect pests, such as nitrogen oxide and sulfur oxide gases and propylene oxide, may also be used to decrease the fitness and increase the metabolic stress on an insect pest during treatment. In some applications, the method may use insecticides, fungicides or bactericides that have a known effect on a particular pest. When used with the low oxygen environment alone or in combination with other stress producing agents, the quantity of pesticide that is required to be used will be less than the quantity that is required to eradicate the pest directly. Accordingly, residues of such pesticides left on the commodity will be negligible or well within acceptable limits.

It can be seen that disinfestation and disinfection effects may be combined and maximized. The combination of the effects of an environment with a low oxygen, high ballast gas atmosphere along with the cycled pressure differential and metabolic stressors allows for virtually complete disinfestation of the commodity. The modified gaseous environment used may also simultaneously induce biocidal effects or microbial growth delay effects lasting a few days or more at room temperature thereby increasing the shelf life of commodity. These microbial control effects can be extended effectively many times longer with the use of refrigerated storage for the commodities.

The shortened time required for effective disinfestation and disinfection, and the use of natural, transient chemicals in the procedure, eliminates or minimizes the potential for sensory and/or physiological changes in the host commodity (i.e. due to anaerobic respiration or fermentation), while the production of residues is largely avoided. In addition, the shortened time makes this method a practical and economical approach over previous attempts to use standard modified atmospheres in foods and in fresh horticultural perishable commodities. Design, engineering, and manufacturing of large, commercial size systems constructed with special materials and functional capabilities are now possible.

According to one aspect of the invention, a method is provided for disinfestation and disinfection of a commodity by depriving an insect or mite of oxygen and introducing metabolic stress in said insect or mite while in an oxygen deprived state.

According to another aspect of the invention a method for controlling an insect, mite or other biological pest is provided comprising exposing a pest to a reduced oxygen environment for a period of time; manipulating the respiratory system of the pest in order to overcome the ability of the pest to establish a reserve of air within collapsible air sacs and then exposing the pest to at least one chemical shown to cause metabolic stress in insects, mites and other biological pests.

Another aspect of the invention provides a method for microbial control, comprising the steps of exposing microbes to an environment of low oxygen high ballast gas concentrations for a period of time and exposing the microbes to at least one metabolically toxic agent while exposed to the anoxic environment.

According to another aspect of the invention, a method is provided for depriving an insect or mite of oxygen and then introducing metabolic stress in the insect or mite while in an oxygen deprived state by subjecting the insects or mites to an oscillating radiofrequency field.

According to another aspect of the invention, a method for controlling an insect, mite or other biological pest is provided that includes exposing a pest to a reduced oxygen environment for a period of time; manipulating the respiratory system of said pest; exposing said pest to a radio frequency field for a period of time and exposing the pest to at least one chemical shown to cause metabolic stress in insects, mites and other biological pests.

An object of the invention is to provide an effective and economical method for disinfestation and disinfection of a commodity that is non-thermal, residue free and a legitimate alternative to methyl bromide fumigation.

A further object of the invention is to provide an effective and inexpensive method for controlling protozoa, parasites and tissue cyst infectious agents.

Another object of the invention is to provide a method of disinfestation that overcomes the ability of insects, mites and other pests to create and maintain a reserve of air in the respiratory system.

Another object of the invention is to provide a method to apply mechanical forces on the respiratory system of a pest that forces the release of stored air and damages the components of the respiratory system while leaving the host commodity undamaged.

Still another object of the invention is to provide a method of simultaneously disinfesting and disinfecting heat sensitive commodities continuously or in batches.

Another object of the invention is to provide a method of disinfestation and disinfection that displaces the acid-base balance in cells with carbon dioxide to lower the pH and cause lethal or sub-lethal effects in the cells and tissues of the pest.

A further object of the invention is to provide a pressure cycled anoxic environment that may also include secondary stress effects with the use of toxic gases, volatile disinfectants or antiseptics to increase the effectiveness of anoxic environment on the pest.

Another object of the invention is to provide secondary stress effects with the use of radio frequencies in oscillating electric fields to both increase the oxygen demands in insects and mites and to generate atomic oxygen and molecular ozone in situ within the enclosed environment.

Another object of the invention is to provide a method of disinfestation and disinfection that has a short duration and can be adapted to treat perishable commodities without changing the chemical properties, the physical characteristics or shortening the shelf life of the commodity.

Another object of the invention is to provide an apparatus and method for disinfestation and disinfection of commodities that is simple to use, easy to construct and inexpensive to purchase and maintain.

Further objects and advantages of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

DETAILED DESCRIPTION OF THE INVENTION

Figure 1:
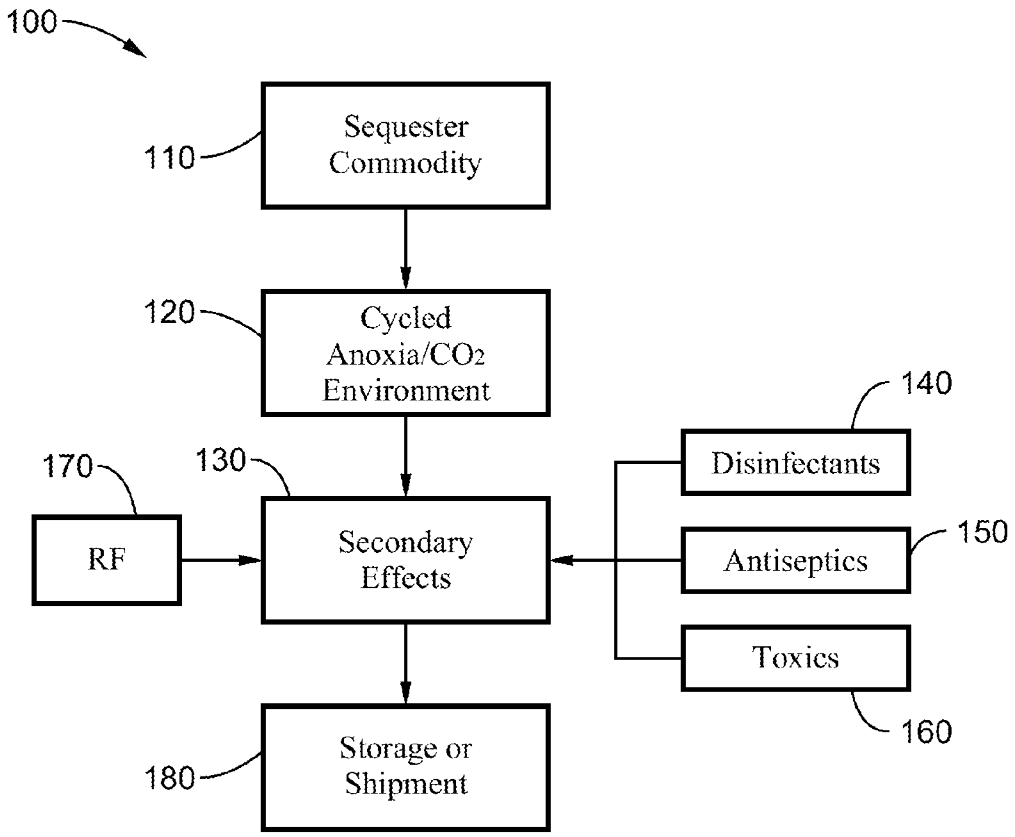
FIG. 1 is a flow diagram of one embodiment of the disinfestation method according to the present invention.
Figure 2:
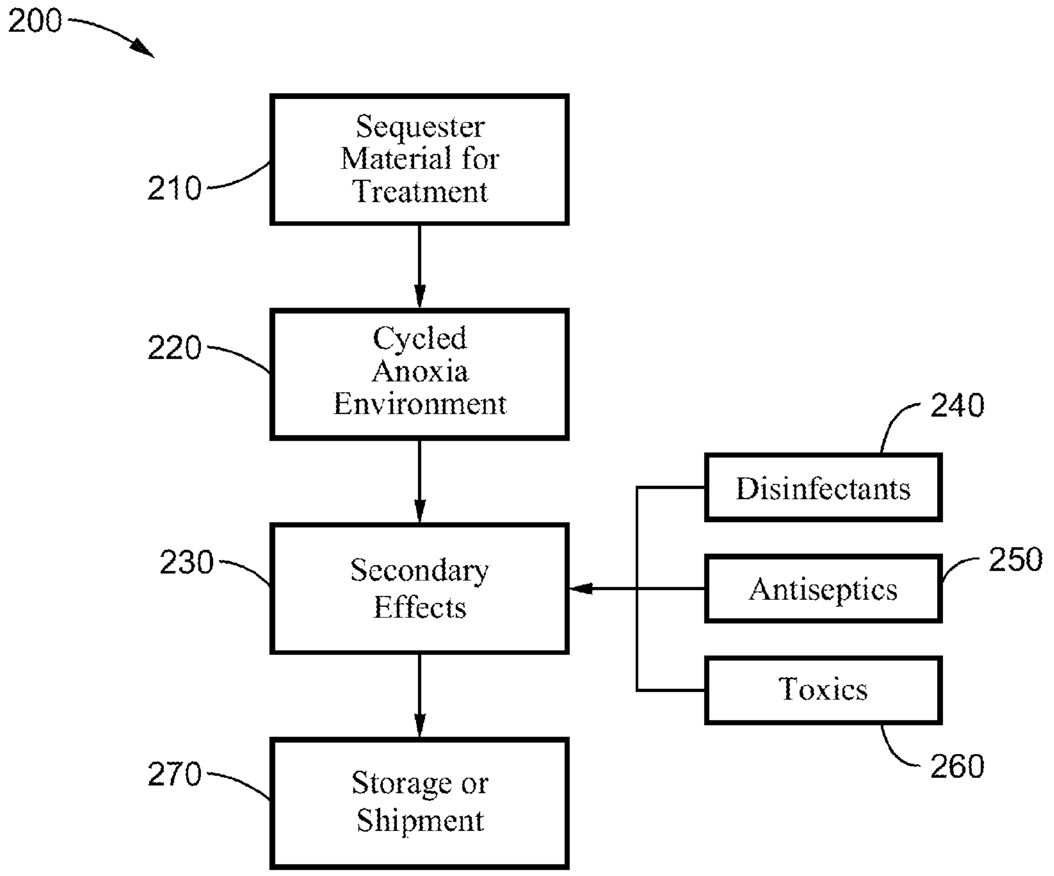
FIG. 2 is a flow diagram of one embodiment of the disinfection method according to the present invention.

Referring more specifically to the drawings, for illustrative purposes the present invention is embodied in the apparatus and method generally shown in FIG. 1 through FIG. 2. It will be appreciated that the apparatus mentioned may vary as to configuration and as to details of the parts, and that the method may vary as to the specific steps and sequence, without departing from the basic concepts as disclosed herein.

A wide variety of commodities may be subject to infestations of insects and other pests during packing, shipment and storage. The methods of the present invention may be particularly beneficial to the disinfestation and disinfection of fresh produce including fruits and vegetables as well as dried foods including nuts; grains; seeds; dehydrated foods including cereals; processed foods; animal feeds; eggs; ornamental and cut flowers; wood products; nursery stocks; agricultural soils including nursery or containerized soils and non food commodities needing disinfestation such as archeological and art objects. Perishable food commodities are often the most difficult to disinfest in the art and are used for illustration of the methods of the present invention.

Agricultural commodities are typically boxed in the field or taken from the fields and packed in a packing plant or stored in a storage facility before being transported to market. Insects and other pests may be present on a commodity in the form of adults as well as egg or larval forms. Quarantine level disinfestation requires eradication of every form of the insect to guarantee that no further pests or damage will appear during transportation and storage of the commodity.

The apparatus and methods of the invention are an effective alternative to methyl bromide that does not leave any toxic residues or damage the cosmetic appearance of the commodity. The methods can also lengthen the shelf life of many commodities in addition to eradicating the biological pests.

Turning now to FIG. 1, a flow diagram of one embodiment 100 of the method for disinfestation of a commodity is generally shown. At block 110, the commodity is sequestered in an enclosure or container. The container or enclosure can be sized and adapted to the type of commodity that is to be treated from single flats to multiple pallets of containers. The container or enclosure is preferably gas tight and configured to remain sealed during positive or negative pressure changes within the interior of the container. In one embodiment, the container has intake and output valves to permit the efficient evacuation and deposition of gasses within the container. In another embodiment, the enclosure is configured to receive multiple pallets and may be room sized. In this embodiment, there may be multiple valves connected to the enclosure to efficiently evacuate and transfer gas or air from the interior of the enclosure as well as manipulate the interior pressure of the enclosure.

At block 120 of FIG. 1, the sequestered commodity is exposed to an anoxic environment for a period of time. The environment that is established in the container preferably has a very low oxygen content to eliminate the source of diffusible oxygen for cellular respiration in insects, mites and microbes etc. It is also preferred that the created environment have a high ballast gas content. In addition, a cycled pressure differential is created within the container for one or more cycles over a period of time to apply mechanical stresses on the respiratory system of the infesting insects.

The type of pest that is to be eradicated and the sensitivity of the commodity to the ballast gases and pressure changes govern the time of exposure to the anoxic environment. The time of exposure is typically less than 24 hours and usually in the range of 1 to 12 hours. The comparatively short treatment times will not pose a significant delay in bringing fresh fruits or vegetables to market. It will be also seen that treated commodities will typically have a greater market life than untreated commodities.

It is preferred that an extremely low oxygen environment of less than 1% oxygen per volume be created in the container or enclosure. An environment of less than approximately 0.01% oxygen per volume is particularly preferred. Oxygen is an essential metabolite for all insects and mites as well as for aerobic microbes and it must be available in the cellular environment in order to sustain vital metabolic activity. All insects and mites, and many microbes, are aerobic organisms utilizing glycolysis, the Kreb's cycle, and electron-transport mechanisms for metabolic reactions leading to the conversion of nutrients (i.e. sugars) into stored chemical energy (ATP). Mortal injuries may be selectively inflicted on pests by preventing the uptake of oxygen and restricting the discharge of carbon dioxide through the respiratory system of the insects while leaving the host commodity unaffected.

The preferred ballast gases are carbon dioxide, nitrogen gas or a combination of carbon dioxide and nitrogen gases. While carbon dioxide or nitrogen gases are preferred, other gases other than oxygen that do not react significantly with the host commodity can be used. It is preferred that the ballast gas in the environment of the container have greater than approximately 99% carbon dioxide or nitrogen gas by volume. A ballast gas concentration of greater than approximately 99.9% by volume is particularly preferred. The use of a high concentration of a ballast gas or combination of gases like carbon dioxide or nitrogen disrupts the flow of any remaining oxygen in the respiratory tract of the insect and may influence the outward exchange of carbon dioxide from the respiratory tissues.

A pressure differential is preferably established with the pressure changes in the environment of the enclosure conducted over one or more cycles. The pressure differential cycles may have a range that is completely hyperbaric, completely hypobaric or a range that is hyperbaric on one extreme and hypobaric on the other. In one embodiment, the pressure differential ranges from −10 to +5 pounds per square inch from the ambient barometric pressure baseline. In another embodiment, the environment is maintained at pressures above the ambient barometric pressure with the pressure differential ranging from +1 to +8 psi. In another embodiment, the container environment is maintained at pressures below the ambient barometric pressure with the pressure differential ranging from −7 to −2 psi. Although these pressure ranges may be preferred, it will be understood that any pressure range can be used that does not damage the commodity and demonstrates a physiological effect on insects, mites and other animals.

The pressure cycles may be conducted after the low oxygen, high ballast gas environment is established in the container. Alternatively, the pressure cycles may begin with the initial purging of the air in the container as the low oxygen environment is established in the container. In this embodiment, the air within the container is preferably removed with several consecutive or time delayed cycles and replaced with ballast gasses to provide an environment that is preferably less than one percent oxygen by volume.

It can be seen that the cycling pressure differential in an established environment or the progression of low pressure (vacuum) and high pressure purging of the environment within the container will eliminate the ability of the insects to establish an air reserve with collapsible sacs in the respiratory system. The airflow in the typical insect respiratory system is controlled in part by muscles that operate flap like valves within each tracheal trunk and spiracle, the opening in the exoskeleton of the insect. In low oxygen or other stress environments, sections of the system of tracheal tubes can collapse to form pockets and provide the insect with a reserve of air. Positive and negative changes in pressure can overcome the air reserve system of the insect so that the insect will not be able to withstand exposure to the low oxygen/high carbon dioxide environment. Mechanical forces from the low-pressure conditions force open the collapsed air sacks in the respiratory system of the insect because of the difference in pressure in the respiratory system with respect to the pressure in the container environment. Forced release of any stored air in the respiratory system will allow the air reserve of the insect to be replaced with a ballast gas thereby upsetting the oxygen equilibrium within the body of the insect.

In addition, during the opposite cycle with increased pressure, gaseous oxygen in the remaining air is diluted with pressurized $CO_2$ and outside forces are created on the spiral cuticles (taenidia) that provide physical support to the connecting tubes of the respiratory system allowing them to remain open or avoid collapse.

Multiple hypobaric/hyperbaric (i.e. vacuum/pressure) cycles are preferably utilized to remove the ambient oxygen in the container and to remove the air reserve in insects and mites as well as provide other physical and chemical stresses on insects while avoiding changes in quality attributes in the host commodity. For example, lower pressure differentials that do not to exceed approximately ±5 psi for short durations can be utilized to minimize potential physical (i.e. texture) damage to sensitive commodities such as wild berries and the like. Other commodities that are not pressure sensitive may have larger pressure differentials than 5 psi with fewer cycles to achieve the desired results.

The amount of oxygen remaining in the entire insect respiratory system (both gaseous and dissolved) is diluted considerably with each pressure cycle according to the principles of Dalton's Law of Partial Pressures. The addition of carbon dioxide or nitrogen ballast gas to the container may also induce changes in the cellular metabolism of the insects or mites. For example the use of carbon dioxide environments may result in changes in the acid-base equilibrium (i.e. pH changes) in cells as well as modify the dissolved/gaseous oxygen balance in the respiratory system. The displacement of the equilibrium between the dissolved oxygen in the insect body and the gaseous oxygen in the respiratory system allows for the nearly complete removal of respiratory oxygen from the insect causing toxic conditions in the body. Similar structural and biological effects are observed in egg, pupae and larval forms of insects or mites.

The commodity is preferably kept in the anoxic environment for a period of time, usually less than 24 hours. Between pressure cycles the container is preferably maintained at or near the barometric pressure of the surroundings to eliminate the potential for the flow of air into the container or gas from the container. A purging cycle of the environment may also be repeated periodically in order to vent any detrimental gases that are formed from metabolic processes in fruits and vegetables in order to minimize the potential for physiological changes in the commodity including anaerobic fermentation. The need for such venting of gases will vary with the characteristics of the commodity.

In order to accelerate mortality and other biological effects on insects, mites and other biological pests, additional secondary effects may be optionally initiated at block 130 of FIG. 1. Stimulated metabolic activity and oxygen demand as well as secondary stresses on the insects and mites accentuate the effect of the anoxic environment and increases mortality. Multiple stressors may produce essentially complete insect mortality as well as reduce the time of exposure of the commodity to the controlled environment. The source of the secondary stress need not be toxic to the insects or mites or delivered at toxic concentrations. However, the combination of an anoxic environment and toxic materials may allow some toxins to be effective at very small concentrations. It is preferred that the sources of the secondary effects leave little or no residues on the commodity.

Secondary effects using metabolically toxic disinfectants such as ozone or hydrogen peroxide that are known to be effective with a specific pest may be created at block 140. Hydrogen peroxide, for example, is an optional disinfectant that can provide metabolic stress to insects and mites in relatively low concentrations leading to mortality while simultaneously inducing disinfection effects. The addition and dispersal of $H_2O_2$ in the enclosure takes advantage of the volatility of hydrogen peroxide in low-pressure conditions ($p_p$=1 mm Hg at 15° C.).

Likewise, antiseptics that can be quickly evaporated within the container or added externally into a reduced pressure environment to allow for their rapid gasification and a complete distribution over the commodity's surface may be added at block 150 of FIG. 1. Although volatile antiseptics and a low pressure environment are preferred, it will be understood that any antiseptic and a neutral or positive pressure environment can be used.

One chemical that has been shown to be effectively dispersed in a low-pressure environment is ethanol. Ethanol (EtOH) and other alcohols are known antiseptics and their action is rapid and effective, especially for plant pathogens like fungi and for human pathogens such as bacteria. Ethanol vapors can also be generated rapidly within a container or be added into a low-pressure container by spraying or may be introduced in the form of vapor by heating to permit rapid and uniform dispersal. Partial pressures of approximately 40 mm of Hg are possible with ethanol in a reduced pressure environment at 15-20° C. Spraying ethanol through nozzles or simply adiabatically expanding hot, liquid ethanol within a container, where it can be rapidly cooled, would also help introduction and dispersion while preventing potential thermal injuries to sensitive commodities.

For example, with one embodiment, disinfestation of fruit flies from a commodity can be accomplished using 10 pressure cycles over a period of an hour with a minimum pressure of approximately −10 psi and a maximum pressure of approximately +1 psi. In this embodiment, the ethanol filling cycle starts with a minimum pressure of −14 psi and adding a 1 psi vapor partial pressure of ethanol. Between pressure cycles, the container is maintained at approximately −12.5 psi.

Ethanol influences the function of the central nervous system in man and it is likely that a similar activity occurs in insects and mites as the use of ethanol combined with anoxia and $CO_2$ has been shown to be highly effective in controlling all developmental phases in various insects and mites. In addition, tests have shown that there are no detectable sensory effects on commodities such as table grapes, blueberries, raspberries, blackberries, oranges, and lemons with the use of ethanol to provide a secondary effect on the metabolism of pests.

Other materials that have been shown to be toxic or metabolic stimulants to pests that are preferably in gas or vapor form may be introduced at block 160 of FIG. 1. For example, the nitrogen oxides and the sulfur oxides have been used effectively. It is preferred that such toxics or metabolic stimulants do not leave a residue if the commodity is for human consumption.

The use of regulated pesticides and fumigants may also be used in some cases. It will be seen that traditional toxic fumigants used at block 160 can be administered in smaller concentrations in combination with the anoxic environment than are customarily required to achieve toxicity alone. The quantity and time of exposure can also be adjusted to limit the appearance of unwanted residues in the commodity.

Alternatively, in one embodiment, oxygen radicals and ozone can be produced in situ within the commodity container preferably using oscillating or pulsed radio frequency fields at block 170 of FIG. 1. One source of pulsed radio frequency fields is found in the apparatus disclosed in U.S. Pat. No. 6,638,475 incorporated by reference herein.

Ozone ($O_3$) is a powerful oxidizing agent that leaves no toxic residue and can be added or generated in situ to further induce toxic effects to cellular metabolism in insects and mites. In situ generation also allows the use of the atomic oxygen precursor of molecular ozone as the initiator of the oxidizing effects of $O_3$. Atomic oxygen, an extremely rapid and reactive radical, is hundreds to thousands of times more reactive than molecular ozone.

Ozone may be formed near surfaces in air voids subjected to an oscillating electrical field being generated by pulsed RF power that provides a high probability for a direct effect on insects, mites, or on microbial contaminants present on the surface. An electric field potential in air of between approximately 3 kV per centimeter to approximately 5 kV per centimeter is usually required to produce ozone at standard temperature and pressure.

In addition, the use of a low oxygen/high ballast gas environment in combination with the use of ozone has a synergistic effect. Therefore, the concentration of molecular ozone that is normally required for disinfestation or disinfection may also be significantly reduced thus avoiding any secondary deleterious effect that may occur due to higher molecular ozone interactions with the host commodity such as oxidation or browning. The combination of the anoxic conditions with ozone (in situ and/or externally produced) allows the disinfestation process to be completed with greater efficiency and in shorter times. Furthermore, using the known disinfection effects of ozone allows disinfestation and disinfection effects to be simultaneously administered.

In addition to removing oxygen and creating a toxic environment, this embodiment of the process may also increase the oxygen demand in insects by applying an oscillating radiofrequency-generated electric field that uses the conductivity of insects and mites to induce polarization effects. The oscillating electric field from a pulsed RF source forces the conductive insect and mites to physically react to the changing field and induces small electric currents within the insects & mites, which results in the formation of dipoles. Polarized insects and mites are forced to react by trying to orient themselves to the changing electric field thus forcing them to increase their activity and accelerate respiratory demands. Accordingly, radio frequency fields can be applied to increase oxygen demands as well as generate reactive oxygen radical or ozone gases.

The enhancement of oxygen demands in insects and mites can also be achieved with increased temperatures above room temperature since increased temperatures force insects and mites to accelerate their metabolism. Increased temperatures may be limited in use to temperature-resistant commodities.

It can be seen that the process has multiple parameters that can be tailored to pests and commodities with a wide range of characteristics. The secondary stress effects that are produced at block 130 using oscillating electrical fields at block 170, disinfectants at block 140, antiseptics at block 150 or other toxics at block 160 can be conducted alone or in combination with the application of one or more of the other secondary stressors. Simple manipulations of the parameters will allow the process to be optimized to particular pests and host commodities and the costs of administering the process can be minimized.

At the end of the treatment period, the commodities are removed from the anoxic environment of the container. The commodities may be treated in the original bins or containers from the field or repackaged after treatment. At block 180 of FIG. 1, the treated commodities are stored or shipped to market. It is preferred that only treated commodities be stored together to avoid re-infestation.

Turning now to FIG. 2, a block diagram of one embodiment of the invention 200 directed to disinfection of commodities from bacterial, fungal, protozoan or other microorganism is shown. The control of microorganisms is one of the major concerns and challenges in food production. The presence of microorganisms on a commodity can result in reduced shelf life and cross contamination during transportation and storage of the host commodity. Controls are needed to retard or prevent spoilage and to reduce or eliminate health hazards associated with foods due to microorganisms. The method 200 can be used for disinfection alone or as part of a disinfestation and disinfection scheme. The method 200 can also be used alone or in conjunction with traditional washing and other disinfection techniques that are presently used in food commodity processing.

At block 210 of FIG. 2, the commodity is sequestered in a preferably gas tight container or enclosure. Agricultural commodities can be processed in containers from the field or may be transferred to containers before processing. The container or enclosure may be sized to accommodate any size or shape of commodity packaging from individual packages to pallets.

The sequestered commodities are exposed to a modified environment created in the container preferably having extremely low oxygen concentrations and high carbon dioxide concentrations for a period of time determined by the type microorganism and the type of commodity at block 220 of FIG. 2. The time of exposure typically ranges from a few minutes to a few hours. The time of exposure can be lengthened if necessary with commodities such as nuts, grains or historical artifacts and the like that are not substantially effected by high concentrations of carbon dioxide.

The preferred oxygen concentrations in the environment of the container are preferably less than approximately 0.1% and carbon dioxide concentrations greater than approximately 99.9%. Oxygen concentrations of less than 0.01% are particularly preferred. Although carbon dioxide is preferred, nitrogen gas or a combination of carbon dioxide and nitrogen gas or other preferably inert ballast gas can be used.

The environment in the container or enclosure is preferably established by using pressure differentials that are applied with a combination of vacuum and purging cycles. Once established, the environment is preferably maintained at or near the atmospheric pressure of the surroundings. The size of the pressure differentials should account for the sensitivity of the commodity to positive or negative atmospheric pressures. The preferred range of pressures is approximately −20 psi to approximately +5 psi. For pressure sensitive commodities, a range of approximately −10 psi to approximately +1 psi is preferred and used in short periods of time in the order of tens of seconds to approximately one minute.

The method described herein combines the benefits of a low oxygen and a high carbon dioxide environment to affect the growth of both aerobic and anaerobic organisms. This is because the process involves a series of environmental manipulations to rapidly change the chemical environment within cells by depriving them of oxygen as well as affecting the acid-base balance and thus forcing an additional toxic effect created with a high $CO_2$ concentration purging the cellular gaseous environment.

As with insects, oxygen is an essential metabolite for the growth of aerobic microorganisms. Depriving cells of the needed oxygen induces metabolic stress and death. The lack of oxygen deprives cells from processing nutrients through oxidation-reduction reactions that are responsible for energy production and synthesis. The elimination of carbon dioxide, an end product of respiration, is also critical to maintaining cell viability and the acid-base balance at neutral pH (~7) required for some microorganisms to survive and grow. However, microorganisms vary widely to their tolerance to carbon dioxide. In a $CO_2$ atmosphere, the growth of some organisms may be suppressed, while others may be less affected.

The created environment with excess $CO_2$ forces pH changes and increases the water activity required for cells to maintain vital metabolic functions. For example, carbon dioxide reacts with water to form carbonic acid ($H_2CO_3$). Carbonic acid reacts chemically with bases forming bicarbonate ($HCO_3^-$), which is the most common chemical form for cells to store carbon dioxide. Normal pH (pH ~7) is regulated with the hydrated form of $CO_2$, that is carbonic acid ($H_2CO_3$), which in turn is rapidly converted to bicarbonate ($HCO_3^-$). Bicarbonate buffering capacity helps provide and maintain a neutral pH balance in cells. Therefore, as is done in this process, a rapid shift of the acid-base balance is created in cells when exposed to high concentrations of $CO_2$. This shift forces a lower pH (near pH 4) in cells causing stress and death to the cells or tissues.

It has been seen that the distribution of gaseous and dissolved carbon dioxide flows from higher to lower pressures (or concentrations). As $CO_2$ is formed within cells, the intracellular carbon dioxide will normally flow to the cell's peripheral spaces where it is expelled through the air transport mechanisms. High concentrations of extra cellular carbon dioxide lead to higher intracellular concentrations of carbon dioxide byproducts. A forced high concentration of intracellular $CO_2$ also results in deleterious effects on cellular metabolism most likely due to the shift of the normal acid-base balance within cells to a more acidic pH range. It also increases the presence or retention of toxic $CO_2$ in the cell while reducing its elimination.

Although some microorganisms may be expected to be more resistant to these combined effects than insects, most microorganisms are affected with lower oxygen and high $CO_2$ environment. Even with relatively short periods of exposure, a reduction of the growth rate of large concentrations (~$10^7$ cfu/mL) of exogenous spoilage organisms (i.e. *Botrytis* sp., *Penicillium* sp., *Phytophthora* sp., *Alternaria* sp. *Rhizopus* sp., etc.) as well as pathogenic bacteria, including *Salmonella thyphimurium, Escherichia coli* O157 H7, and *Staphylococcus aureus* have been demonstrated simultaneously with the disinfestation effects described herein.

To increase the mortality rate or extend the growth rate delays of fungal organisms, bacteria and other microorganisms, the commodities are optionally treated with disinfectants, antiseptics or other materials that are toxic to microorganisms or shown to increase the effect of the anoxic environment at block 230 of FIG. 2. The materials that are selected for use at block 230 preferably do not leave a residue on the commodity that is toxic to humans and can be distributed in gas, vapor or aerosol form to the sequestered commodities. The materials that are selected for use can be directed at a particular microorganism and the sensitivity of a particular commodity to the material, if any.

A reduced pressure modified low oxygen environment is preferably used to create and distribute volatile chemicals with known disinfection properties at block 240, or known antiseptic properties at block 250 or other toxic properties at block 260 of FIG. 2. Although a reduced pressure environment is preferred, the secondary effects at block 230 can be achieved with the introduction of disinfectants 240, antiseptics 250 or other toxics 260 at a neutral or positive pressure in the container. It will also be understood that more than one disinfectant can be added to the anoxic environment sequentially or simultaneously at block 240 of FIG. 2. Similarly, a disinfectant and an antiseptic or toxic material can be added to the anoxic environment alone or in combination to achieve the desired effect.

One of the natural, short lived or easily removed chemicals that can be used as a disinfectant at block 240 of FIG. 2, is ozone ($O_3$) added from external sources or generated in situ from its atomic (radical) oxygen precursor (O.) using RF techniques. Ozone is a powerful oxidizing agent that has a direct biocidal and biostatic effect on microorganisms. The amount of ozone that is normally required to disinfect surfaces can be greatly reduced due to the synergistic effect of the anoxic atmosphere and the ozone on microorganisms.

In addition, low-level concentrations of hydrogen peroxide $H_2O_2$ (<1 g/L) of (10-30% v/v; m.p. −0.9° C.; $p_p$=1 mm at 15° C.) have been used alone and in combination with other antiseptics to eliminate or suppress microbial growth. Hydrogen peroxide is useful because of its volatility in low-pressure conditions as well as its disinfection capabilities. Although ozone and hydrogen peroxide are preferred disinfectants, other antiseptics, including ethylene oxide and propylene oxide, may be used alone or in combination with other materials.

Likewise, antiseptics such as ethanol or other alcohols are effective at controlling plant pathogens such as fungi, protozoa and bacteria. Antiseptics can be used alone or in combination with other antiseptics, disinfectants or toxics at block 250 of FIG. 2 to bolster the biocidal and biostatic effect of the anoxic environment that is created at block 220.

One particularly useful combination of volatile chemicals is approximately 30% hydrogen peroxide and approximately 70% ethanol by volume introduced to the anoxic environment produced at block 220 of FIG. 2. This combination is beneficial for both disinfection and disinfestation because of the disinfectant characteristics as well as the deleterious effects on the metabolism of insects and mites.

The method at block 260 of FIG. 2 also allows for the use of other chemicals known for their rapid effects on microorganisms, singly or in combination. For example, gases of the group of nitrogen oxides or of sulfur oxides, which have been used in some food processing applications, may be used in addition to the anoxic environment. Sulfur dioxide ($SO_2$) for example, is a fumigant that is particularly useful in the control of fungal organisms. However, its use may be limited by existing regulatory limits for residues in foods (i.e. <10 ppm) due to the fact that it induces the formation of sulfites, a chemical known to have adverse effects in certain sectors of the human population. Sulfur dioxide is also used extensively in the food industry as a bleaching agent.

Other regulated and non-regulated bactericides and fungicides may also be used on commodities at block 260 of FIG. 2 depending on the nature of the commodity and the types of microorganisms that are prevalent. The combination of the low oxygen and high carbon dioxide environment and secondary bactericides or fungicides allows smaller quantities of secondary materials to be used to achieve the desired results. Consequently, the volume of bactericide or fungicide that is applied may be substantially less than is required to kill or delay the growth of pests when used alone. Therefore, the residues that may be present at block 260 will be substantially smaller and within acceptable limits for human or animal consumption.

Accordingly, the biocidal or biostatic effect on microorganisms of the low oxygen-high carbon dioxide or other ballast gas environment created at block 220 can be enhanced with the use of volatile disinfectants 240 or antiseptics 250 such as ozone, ethanol, or hydrogen peroxide used singly or in combination. The use of these materials may also reduce the time of exposure of the commodity to the anoxic environment as well as the overall processing time for disinfection within the range of several seconds to minutes.

It can also be seen that the effect of a low oxygen and high carbon dioxide environment contributes and combines to induce rapid mortality in insects while simultaneously causing metabolic biocidal or biostatic effects on microorganisms. Since exogenous fungal and pathogenic organisms are usually present in perishable food commodities, microorganisms can also be treated along with insects by the controlled environment as oxygen and carbon dioxide are critically related to their cellular metabolism and survival.

As a result of the process, the rate of microbial growth is eradicated or decreased significantly allowing for a longer shelf life of the commodity, which can be further extended under refrigerated storage. Disinfection effects have also been shown in injured fruit leading to biocidal and/or biostatic effects.

After exposure to the controlled environment for a sufficient period of time, the commodities are removed from the closed container at block 270 of FIG. 2 and prepared for shipping or storage. Traditional handling, storage and shipping of treated commodities can be used if care is taken to avoid re-infection.

The invention may be better understood with reference to the accompanying examples, which are intended for purposes of illustration only and should not be construed in any sense as limiting the scope of the present invention as defined in the claims appended hereto.

Samples of insects and mites including various types of Thrips (*Frank—liniella occidentalis*), Fruit Flies (*Drosophila melanogaster*), Ants (*Pogonomyrmex subdentata*), Aphids (*Myzus persicae*), Harlequin Bugs (*Murgantia histrionica*), and Mites (*Amblyseius cucumeris, Tetranychus urticae*) were used to demonstrate the disinfestation capabilities of low (hypobaric) or high (hyperbaric) pressure low oxygen and high carbon dioxide concentration environments on a variety of insect pests. The addition of antiseptics, disinfectants and radio frequency (RF) and ozone to the anoxic environment was also used on infestations of mites and other pests. Treated and non-treated (control) samples for some insects included all mobile life cycles (i.e. juvenile, adults, pupas, larva, etc.) as well as eggs.

EXAMPLE 1

Experiments involving a hypobaric condition were conducted with a Precision Vacuum Oven (PVO) provided with a manometer (−30 inches of Hg to +15 psi range) and internal Hg thermometer and were modified to allow for vacuum and pressurized purging operations with different gas mixtures. A dry pump was used to establish vacuum up to −14 psi (−724 mm Hg). Purging was conducted with carbon dioxide up to reaching barometric pressures or slightly below (−1 psi). Carbon Dioxide was used as a source for purging and for establishing the high concentration carbon dioxide environments. Nitrogen gas was also used as an inert ballast gas to utilize different $CO_2$ gas environments to establish the proper conditions in some experiments.

The effect of a low oxygen/high carbon dioxide environment at below the ambient barometric pressure on Ants, Mites, Thrips, Harlequin Bugs, Aphids, Fruit Flies at different stages of development was evaluated. It can be seen that the controlling effect of an anoxic hypobaric carbon dioxide environment on mortality of the subject insects is significant. Observations of the hypobaric treatments were made immediately after the treatment and mortality was observed 24 hours after the treatment.

Control of adult Ants in a hypobaric environment with at least one pressure cycle is found in Table 1. In one experiment the Ants were totally immobilized and eradicated with an 8-hour treatment.

Significant mortality in adult and juvenile mites as well as Mite eggs with hypobaric treatments was seen in the results in Table 2 through Table 5. Sizeable pressure changes alone in a low oxygen atmosphere were not as effective as minor pressure changes in a low oxygen high carbon dioxide environment. Greater than 90 percent mortality for adult and juvenile Mites was observed with treatment times in the range of 4 to 7 hours with a pressure differential of −2 psi.

Adult Harlequin Bugs and Aphids are particularly susceptible to the hypobaric method, as total mortality was seen after seven hours of treatment as shown in Table 6 and Table 7 respectively.

Fruit fly adults had significant mortality 24 hours after treatment as seen in Table 8 with treatment times from 7 to 9 hours. Short duration pressure changes with a minor pressure differential were seen to be effective.

Tables 9 through 11 show the effect of the hypobaric treatments on Thrip adults, pupas and eggs. Eight-hour treatment times were seen to be effective for adult and pupa thrips but only marginally effective on the viability of Thrip eggs.

EXAMPLE 2

To demonstrate the effectiveness of the procedure in a hyperbaric environment, experiments were conducted with a pressure chamber (PC) fitted with a manometer (0 to +15 psi) and proper on/off valves. The chamber was capable of withstanding 5-10 psi pressure without major gas losses for over a 24-hour period.

Purging was conducted in multiple cycles with a high-pressure carbon dioxide flow directly from 2,500-psi storage cylinders at room temperature. Pressure (+2 to +5 psi) was determined with manometers and provided a rapid purge of the pressure chamber environment containing the samples to be treated. During purging, a carbon dioxide/Air volume ratio greater than 3 was used to assure proper air removal.

Table 12, shows the effects of the treatment at hyperbaric pressures on adult ants with three short duration hyperbaric pressure cycles. The Ants show a greater resistance to the hyperbaric anoxic conditions that to the hypobaric treatments.

Control of different species of Mites at various stages of development from egg to adult to cycled hyperbaric anoxic conditions is shown in Tables 13 through Table 17. The results illustrate significant mortality after 24 hours in adult and juvenile mites that have had 6 to 7 hour exposures with a small number of short duration pressure cycles. Mite eggs had 80% mortality after a 6-hour exposure and it is expected that longer exposure times will increase mortality of mite eggs.

Similarly, total mortality was seen in Harlequin Bugs and Aphids as shown in Table 18 and Table 19 respectively. Total mortality was shown in 7 and 8-hour exposures with three short duration hyperbaric pressure cycles.

Table 20 shows the control of fruit fly adults after a 7 to 9 hour exposure to the hyperbaric treatment environment. Greater than 90% mortality can be achieved with three short duration hyperbaric pressure cycles.

The control of Thrips in egg, pupae and adult stages are shown in Tables 21-23. Greater than 90% mortality was observed in adults, pupas and eggs with five short duration pressure cycles.

It can be seen that a wide variety of insects and mites in various forms can be eliminated with the cycling of hyperbaric or hypobaric pressures of a low oxygen/high carbon dioxide environment. Time of exposure to the environment is less than 24 hours and typically less than 8 hours.

EXAMPLE 3

A demonstration of the effect of a low oxygen-high ballast gas environment with a pressure differential with cycles of below barometric pressure to above barometric pressure and a metabolic stressor on fruit flies was conducted for a short treatment time of one hour. The deleterious effects of hypobaric and hyperbaric conditions with an anoxic environment and the presence of ethanol to provide additional metabolic stress were observed with fruit flies at all biological stages. The various biological forms of fruit flies were exposed to a low oxygen-high carbon dioxide environment with 10 cycles of a pressure differential ranging from −20 inches of Hg to +2 inches of Hg for a one hour treatment period. Ethanol vapor at 1.3 to 2.0 in Hg vapor pressure was introduced to the environment as a metabolic stressor. The results are shown in Table 24. It can be seen that adult, pupa, larval and egg forms of fruit flies were completely eradicated with a one hour treatment period. The survival rate for eggs was determined by enclosion rates at beyond 24 hours.

EXAMPLE 4

The effect of secondary metabolic stress mechanisms on pests in a hyperbaric anoxic environment was demonstrated on the juvenile and adult mites. Experiments with pulsed RF fields were conducted with a laboratory-scale system fitted with a parallel-plate capacitor powered with 15 kV NC external transformer. Oscillating electric fields with >5 kV/cm were thus utilized in these combined experiments.

Table 25 illustrates the control of juvenile and adult mites with the secondary stress exerted by a 60 Hz frequency. It can be seen that the addition of a secondary stressor increases the mortality of juvenile and adult mites over the anoxia treatment alone.

EXAMPLE 5

The synergistic effect of pulsed RF fields and a transient toxic gas such as molecular ozone to the eggs as well as juvenile and adult mites is demonstrated in the combined results shown in Table 26. Experiments with atomic oxygen and/or molecular ozone were conducted in a separate laboratory-scale system also fitted with a parallel-plate capacitor powered with a 15 kV A/C RMS external transformer. In these experiments, in situ production of atomic oxygen and molecular ozone took place within the parallel-plate capacitor with oscillating electric fields >5 kV/cm. Parallel, comparison experiments involving molecular ozone were conducted with an external ozone generator feeding the parallel-plate capacitor system thus combining RF and Ozone interactions.

It can be seen that the combination of oscillating electric fields to increase oxygen demand and toxic gases such as atomic oxygen or ozone within a cycled carbon dioxide anoxic environment results in essentially total mortality in the eggs, juvenile and adult forms of Mites.

EXAMPLE 6

Microbial growth rates (i.e. inhibition or retardation) at room temperature have been observed in several molds and bacteria pathogens when exposed to the anoxic conditions (i.e. hyperbaric or hypobaric anoxia with high carbon dioxide environment) as provided for insect disinfestation. In order to document these effects, experiments were carried out with *Botrytis cinerea, Penicillium italicum, Alternaria alternata, Salmonella thyphimurium*, and *Escherichia coli* O157:H7.

Inoculum concentrations ranging from $10^2$ to $10^7$ cfu/mL were plated onto culture plates containing an appropriate growth media, dried in a laminar flow hood, and exposed to the anoxic/carbon dioxide environment. After completion of the exposure time to the regulated gaseous environment, the plates were removed and placed on closed containers for incubation at room temperature (~22° C.). Observations and assays of microbial populations were conducted periodically over subsequent days.

Microbial assays for *Botrytis cinerea* ($10^3$ cfu/mL) treated with cycled anoxic/high carbon dioxide environs for 16 hours at hyperbaric and hypobaric pressures were conducted. Initial growth in treated plates started approximately 2-2.5 days after treatment while growth in the control plates was immediate. It was observed that the hyperbaric process was more effective in causing the growth inhibition effect than the hypobaric process under the conditions tested. Colony counting indicated approximately a 300 times lower population in treated samples over the control samples.

Microbial assays for *Penicillium italicum* ($10^7$ cfu/mL) treated with anoxic/high carbon dioxide environment according to the invention for 16 hours at hyperbaric and hypobaric pressures were also conducted. Initial growth in treated plates started approximately 1-1.5 days after treatment while growth in the control plates was immediate. Colony counting at this time indicated an approximately 1,000 times lower population in treated samples, with the hyperbaric process being approximately 10 times better than the effects with the hypobaric process.

Assays for *Alternaria alternata* ($10^6$ cfu/mL) treated with anoxic/high carbon dioxide environments for 16 hours at hyperbaric and hypobaric pressures were also conducted. No growth in treated plates was observed after approximately 3-3.5 days after treatment.

Microbial assays for *Salmonella thyphimurium* ($10^2$ cfu/mL) treated with anoxic/high carbon dioxide environments for 16 hours at hyperbaric and hypobaric pressures were also conducted. No growth was observed in the treated plates one day after processing. At the onset of growth, colony counting indicated that there were no differences in the number of colonies. However, a significant difference in the stage of development of the colonies compared to the control was observed.

EXAMPLE 7

The addition of low concentrations of a vaporized disinfectant to the anoxic/high carbon dioxide environment has been shown to effectively eliminate some fungi and bacteria with the methods of the present invention. The biocidal effect at room temperature of the method was demonstrated with several fungi and bacteria pathogens exposed to an anoxic & ethanol environment using identical processing as for disinfestation described previously. Experiments were carried out with plant pathogens such as *Alternaria alternata, Rhizopus* sp., and *Penicillium* sp, as well as with human pathogens such as *Salmonella* sp., *Escherichia coli* O157:H7, and *Staphylococcus aureus*.

Generally, inoculum concentrations ranging from $10^4$ to $10^5$ cfu/mL were plated onto culture plates containing an appropriate growth media, dried in a laminar flow hood, and exposed to the anoxia & ethanol environments. After completion of the exposure time to the regulated gaseous environment, the culture plates were removed and placed on closed containers for incubation at room temperature (~22° C.). Observations and assays of microbial populations were conducted periodically over subsequent days.

Microbial assays for *Alternaria alternata* ($10^4$ cfu/mL) treated with an environment of anoxic/high carbon dioxide and low concentrations of 70% vaporized ethanol and 30% of vaporized hydrogen peroxide for 6 hours did not produce any growth in treated plates when observed approximately 6 days after treatment. The control plates were essentially covered with growth after 6 days.

Microbial assays of *Rhizopus* sp. ($10^4$ cfu/mL) treated with an environment of anoxic/high carbon dioxide and low concentrations of 70% vaporized ethanol and 30% of vaporized hydrogen peroxide for 6 hours were conducted. After 6 days, no growth was observed in the treated plates and the control plates were virtually covered with growth.

Similarly, microbial assays of *Penicillium* sp ($10^4$ cfu/mL) treated with an environment of anoxic/high carbon dioxide and low concentrations of 70% vaporized ethanol and 30% of vaporized hydrogen peroxide for 6 hours did not produce any growth in the treated plates while the control plates were covered after 6 days.

Microbial assays of *Salmonella* sp. ($10^5$ cfu/mL) treated with an environment of anoxic/high carbon dioxide and low concentrations of 70% vaporized ethanol and 30% of vaporized hydrogen peroxide for 6 hours were conducted. After 4 days, no growth was observed in the treated plates and the control plates exhibited substantial growth.

Likewise, Microbial assays of *Escherichia coli* O157:H7 ($10^5$ cfu/mL) and *Staphylococcus aureus* ($10^5$ cfu/mL) treated with an environment of anoxic/high carbon dioxide and low concentrations of 70% vaporized ethanol and 30% of vaporized hydrogen peroxide for 6 hours produced no growth.

EXAMPLE 8

The capability of the method for disinfection of the surfaces of several fresh fruits was evaluated. Raspberries, blackberries, table grapes, and strawberries were selected since these fruits are often infected with natural flora and can spoil rapidly within a few days if kept at room temperature. Healthy, non-injured fruit was chosen from batches of commercial quality fruit. Control and treated samples from the same batch were kept at room temperature (~22° C.) in sterile dishes and at a laminar flow hood without ventilation. Daily observations were made for the onset and propagation of infective sites.

Raspberries were treated with an environment of anoxic/high carbon dioxide and low concentrations of 70% vaporized ethanol. The time of treatment was 48 hours. After 11 days the control fruit was fully engulfed with natural flora while the treated berries showed no sign of growth.

Blackberries and strawberries were also treated with an environment of anoxic/high carbon dioxide and low concentrations of 70% vaporized ethanol with a treatment time of 48 hours and the treated fruit showed no sign of growth of natural flora when observed 11 days after treatment. The control fruit showed significant growth of natural flora.

Finally, table grapes were also treated with an environment of anoxic/high carbon dioxide for 16 hours and low concentrations of 70% vaporized ethanol for 2 hours. After 7 days at room temperature the control grapes were covered with a substantial growth of natural flora while the treated grapes showed no signs of growth.

EXAMPLE 9

The potential of the method to disinfect injured fruit tissues and affect the development of microbial inoculums was evaluated. Post harvest infections through injury are believed to be the cause of a large fraction of spoilage losses in agriculture.

As discussed previously, one embodiment of the present methods provides a reduced pressure environment particularly suited for expanding or volatilizing some chemical disinfectants with relatively high partial pressures such as ethanol or hydrogen peroxide or to introduce other gases or pesticides into the environment of the container. The tests were conducted with inoculated and injured fruits that were later subjected to the cycled low oxygen/high carbon dioxide environment.

The biostatic effect of the method on *Penicillium digitatum* in fresh Valencia oranges was shown. Oranges were punctured (1×3 mm deep) during inoculation ($10^6$ cfu/mL) thereby allowing the inoculation to reach layers of tissue under the skin. The injury remained partially open during the treatment. The treated oranges were treated with an environment of anoxic/high carbon dioxide for 45 minutes. The treated and control oranges were stored at room temperature. The control oranges exhibited substantial growth of *Penicillium digitatum* within six days of inoculation. No growth was observed on the treated oranges. Results indicated that the treatment method is capable of either reducing microbial growth (a biostatic effect) or causing disinfection (biocidal effects) to both plant and human pathogens.

Accordingly, it will be seen that this invention provides an effective and efficient apparatus and method for disinfesting commodities of insects, mites and other organisms and is a viable alternative to the use of methyl bromide fumigation. It will also be seen that the inventions provides an effective apparatus and method for disinfecting commodities from bacterial, fungal and other microbial pests.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for.

TABLE 1

Control of Ants in a Hypobaric Anoxic/High Carbon Dioxide (−2 psi) Environment

| Time (hours) | Treatment Parameter (Hypobaric) | Effect After Treatment | Mortality 24 h later |
|---|---|---|---|
| 15 h | under vacuum (−28 psi) | 100% immobilized | >80% |
| 17 h | $CO_2$ (−2 psi) | 90% immobilized | >90% |
| 19 h | $CO_2$ (−2 psi) | 90% immobilized | 100% |
| 7 h | $CO_2$ (−2 psi) | 90% immobilized | >90% |
| 15 h | $CO_2$ (−2 psi) | 100% immobilized | >80% |
| 8 h | $CO_2$ (−2 psi) | 100% immobilized | 100% |

TABLE 2

Control of "Thripex" Mites (*Amblyseius cucumeris*) in a Hypobaric Anoxic/High Carbon Dioxide (−2 psi) Environment

| Time (hours) | Treatment Parameter (Hypobaric) | Effect After Treatment | Mortality 24 h later |
|---|---|---|---|
| 15 h | vacuum (−28 psi) | >50% immobilized | >50% |
| 4.5 h | $CO_2$ (−2 psi) | >90% immobilized | >95% |
| 17 h | $CO_2$ (−2 psi) | >80% immobilized | >95% |
| 19 h | $CO_2$ (−2 psi) | >90% immobilized | >98% |
| 7 h | $CO_2$ (−2 psi) | >90% immobilized | >99% |
| 7 h | $CO_2$ (−2 psi) | 100% immobilized | >90% |
| 15 h | $CO_2$ (−2 psi) | 100% immobilized | >98% |
| 6.5 h | $CO_2$ (−2 psi) | 100% immobilized | >95% |

TABLE 3

Control of Adult Mites (*Tetranychus urticae*) with a Hypobaric Anoxic/High Carbon Dioxide (−2 psi) Environment

| Time (hours) | Treatment Parameter | Hypobaric Cycles | After Treatment | Mortality 24 h later |
|---|---|---|---|---|
| 8 h | $CO_2$ | 4 min. 5 purge w/$CO_2$ | 100% immobilized | 95% (95/100) |
| 8 h | $CO_2$ | 4 min. 5 purge w/$CO_2$ | 100% immobilized | 94% (94/100) |

TABLE 4

Control of Juvenile Mites (*Tetranychus urticae*) with a Hypobaric Anoxic/High Carbon Dioxide (−2 psi) Environment

| Time (hours) | Treatment Parameter | Hypobaric Cycles | After Treatment | Mortality 24 h later |
|---|---|---|---|---|
| 6 h | $CO_2$ | 4 min. 5 purge w/$CO_2$ | 100% immobilized | 90% (180/200) |
| 6 h | $CO_2$ | 4 min. 5 purge w/$CO_2$ | 100% immobilized | 90% (180/200) |

TABLE 5

Control of Mite Eggs (*Tetranychus urticae*) with a Hypobaric Anoxic/High Carbon Dioxide (−2 psi) Environment

| Time (hours) | Treatment Parameter | Hypobaric Cycles | After Treatment | Mortality 24 h later |
|---|---|---|---|---|
| 6 h | $CO_2$ | 4 min. 5 purge w/$CO_2$ | N/A | >80% |
| 6 h | $CO_2$ | 4 min. 5 purge w/$CO_2$ | N/A | >90% |

TABLE 6

Control of "Harlequin Bugs" (*Murgantia histrionica*) in a Hypobaric Anoxic/High Carbon Dioxide (−2 psi) Environment

| Time (hours) | Treatment Parameter (Hypobaric) | Effect After Treatment | Mortality 24 h later |
|---|---|---|---|
| 18 h | $CO_2$ (−2 psi) | 80% immobilized | 100% |
| 6 h | $CO_2$ (−2 psi) | 80% immobilized | 80% |
| 19 h | $CO_2$ (−2 psi) | 100% immobilized | 100% |
| 7 h | $CO_2$ (−2 psi) | 100% immobilized | 100% |
| 8 h | with CO2 (−2 psi) | 100% immobilized | 100% |

TABLE 7

Control of Various Aphids in a Hypobaric Anoxic/High Carbon Dioxide (−2 psi) Environment

| Time (hours) | Treatment Parameter (Hypobaric) | Effect After Treatment | Mortality 24 h later |
|---|---|---|---|
| 6 h | $CO_2$ (−2 psi) | 100% immobilized | 100% |
| 19 h | $CO_2$ (−2 psi) | 100% immobilized | 100% |
| 7 h | $CO_2$ (−2 psi) | 100% immobilized | 100% |
| 7 h | $CO_2$ (−2 psi) | 100% immobilized | 100% |
| 8 h | $CO_2$ (−2 psi) | 100% immobilized | 100% |

TABLE 8

Control of Adult Fruit Flies (*Drosophila melanogaster*) with a Hypobaric Anoxic/High Carbon Dioxide (−2 psi) Environment

| Time (hours) | Treatment Parameter | Hypobaric Cycles | After Treatment | Mortality 24 h later |
|---|---|---|---|---|
| 7 h | $CO_2$ | 1 min. 3 purge with $CO_2$ | 100% immobilized | 76% (53/70) |
| 8 h | $CO_2$ | 1 min. 3 purge with $CO_2$ | 100% immobilized | 90% (73/80) |
| 9 h | $CO_2$ | 1 min. 3 purge with $CO_2$ | 100% immobilized | 94% (75/80) |
| 9 h | $CO_2$ | 1 min. 3 purge with $CO_2$ | 100% immobilized | 90% (45/50) |

TABLE 9

Control of Adult Thrips (*Frankliniella occidentalis*) with a Hypobaric Anoxic/High Carbon Dioxide (−2 psi) Environment

| Time (hours) | Treatment Parameter | Hypobaric Cycles | After Treatment | Mortality 24 h later |
|---|---|---|---|---|
| 8 h | $CO_2$ | 3 min. 5 purge with $CO_2$ | 100% immobilized | 96% (192/200) |
| 7 h | $CO_2$ | 3 min. 5 purge with $CO_2$ | 100% immobilized | 80% (160/200) |

TABLE 10

Control of Pupa Thrips (*Frankliniella occidentalis*) with a Hypobaric Anoxic/High Carbon Dioxide (−2 psi) Environment

| Time (hours) | Treatment Parameter | Hypobaric Cycles | After Treatment | Mortality 24 h later |
|---|---|---|---|---|
| 8 h | $CO_2$ | 3 min. 5 purge with $CO_2$ | 100% immobilized | 90% (180/200) |

TABLE 11

Control of Thrip Eggs (*Frankliniella occidentalis*) with a Hypobaric Anoxic/High Carbon Dioxide (−2 psi) Environment

| Time (hours) | Treatment Parameter | Hypobaric Cycles | After Treatment | Mortality 24 h later |
|---|---|---|---|---|
| 8 h | $CO_2$ | 3 min. 5 purge with $CO_2$ | N/A | 50% (125/250) |

TABLE 12

Control of Adult Ants (*Pogonomyrmex subdentata*) With a Hyperbaric Anoxic/High Carbon Dioxide (+5 psi) Environment

| Time (hours) | Treatment Parameter | Hyperbaric Cycles | After Treatment | Mortality 24 h later |
|---|---|---|---|---|
| 7 h | $CO_2$ | 3 pressurized, 1 min. | 100% immobilized | 80% (4/5) |
| 15 h | $CO_2$ | 3 pressurized, 1 min. | 100% immobilized | 60% (3/5) |

TABLE 13

Control of Adult Mites (*Tetranychus urticae*) With a Hyperbaric Anoxic/High Carbon Dioxide (+5 psi) Environment

| Time (hours) | Treatment Parameter | Hyperbaric Cycles | After Treatment | Mortality 24 h later |
|---|---|---|---|---|
| 6 h | $CO_2$ | 5 pressurized, 1 min. | 100% immobilized | 99% (198/200) |
| 6 h | $CO_2$ | 5 pressurized, 1 min. | 100% immobilized | 93% (107/115) |

TABLE 14

Control of Adult Mites (*Amblyseius cucumeris*) With a Hyperbaric Anoxic/High Carbon Dioxide (+5 psi) Environment

| Time (hours) | Treatment Parameter | Hyperbaric Cycles | After Treatment | Mortality 24 h later |
|---|---|---|---|---|
| 7 h | $CO_2$ | 3 pressurized, 1 min. | >90% immobilized | 98% (98/100) |
| 7 h | $CO_2$ | 3 pressurized, 1 min. | >90% immobilized | 90% (180/200) |
| 15 h | $CO_2$ | 3 pressurized, 1 min. | >98% immobilized | 98% (196/200) |

TABLE 15

Control of Juvenile Mites (*Tetranychus urticae*) With a Hyperbaric Anoxic/High Carbon Dioxide (+5 psi) Environment

| Time | Treatment Parameter | Hyperbaric Cycles | After Treatment | Mortality 24 h later |
|---|---|---|---|---|
| 6 h | $CO_2$ | 5 pressurized, 1 min. | 100% immobilized | 90% (90/100) |
| 6 h | $CO_2$ | 5 pressurized, 1 min. | 100% immobilized | 90% (115/125) |

TABLE 16

Control of Mite Eggs (*Tetranychus urticae*) With a Hyperbaric Anoxic/High Carbon Dioxide (+5 psi) Environment

| Time | Treatment Parameter | Hyperbaric Cycles | After Treatment | Mortality 24 h later |
|---|---|---|---|---|
| 6 h | $CO_2$ | 5 pressurized, 1 min. | N/A | 80% (240/300) |

TABLE 17

Control of Adult Mites (*Amblyseius cucumeris*) With a Hyperbaric Anoxic/High Carbon Dioxide (+5 psi) Environment

| Time | Treatment Parameter | Hyperbaric Cycles | After Treatment | Mortality 24 h later |
|---|---|---|---|---|
| 7 h | $CO_2$ | 3 pressurized, 1 min. | >90% immobilized | 98% (98/100) |
| 7 h | $CO_2$ | 3 pressurized, 1 min. | >90% immobilized | 90% (180/200) |
| 15 h | $CO_2$ | 3 pressurized, 1 min. | >98% immobilized | 98% (196/200) |

TABLE 18

Control of Adult Harlequin Bugs (*Murgantia histrionica*) With a Hyperbaric Anoxic/High Carbon Dioxide (+5 psi) Environment

| Time | Treatment Parameter | Hyperbaric Cycles | After Treatment | Mortality 24 h later |
|---|---|---|---|---|
| 19 h | $CO_2$ | 3 pressurized, 1 min. | 100% immobilized | 100% |
| 7 h | $CO_2$ | 3 pressurized, 1 min. | 100% immobilized | 100% |
| 8 h | $CO_2$ | 3 pressurized, 1 min. | 100% immobilized | 100% |

TABLE 19

Control of Adult Aphids (*Myzus persicae*) And Adult Thrips (*Frankliniella occidentalis*) With a Hyperbaric Anoxic/High Carbon Dioxide (+5 psi) Environment

| Time | Treatment Parameter | Hyperbaric Cycles | After Treatment | Mortality 24 h later |
|---|---|---|---|---|
| 19 h | $CO_2$ | 3 pressurized, 1 min. | 100% immobilized | 100% (30/30) |
| 7 h | $CO_2$ | 3 pressurized, 1 min. | 100% immobilized | 100% (30/30) |
| 7 h | $CO_2$ | 3 pressurized, 1 min. | 50% immobilized | 100% (30/30) |
| 8 h | $CO_2$ | 3 pressurized, 1 min. | 100% immobilized | 100% (30/30) |

TABLE 20

Control Adult of Fruit Flies (*Drosophila melanogaster*) With a Hyperbaric Anoxic/High Carbon Dioxide (+5 psi) Environment

| Time | Treatment Parameter | Hyperbaric Cycles | After Treatment | Mortality 24 h later |
|---|---|---|---|---|
| 7 h | $CO_2$ | 3 pressurized, 1 min. | 100% immobilized | 80% (48/60) |
| 8 h | $CO_2$ | 3 pressurized, 1 min. | 100% immobilized | 90% (73/80) |
| 9 h | $CO_2$ | 3 pressurized, 1 min. | 100% immobilized | 94% (75/80) |
| 9 h | $CO_2$ | 3 pressurized, 1 min. | 100% immobilized | 90% (45/50) |

TABLE 21

Control of Adult Thrips (*Frankliniella occidentalis*) With a Hyperbaric Anoxic/High Carbon Dioxide (+5 psi) Environment

| Time | Treatment Parameter | Hyperbaric Cycles | After Treatment | Mortality 24 h later |
|---|---|---|---|---|
| 8 h | $CO_2$ | 5 pressurized, 1 min. | 100% immobilized | 90% (180/200) |
| 7 h | $CO_2$ | 5 pressurized, 1 min. | 100% immobilized | 95% (190/200) |

TABLE 22

Control of Thrip Pupas (*Frankliniella occidentalis*) With a Hyperbaric Anoxic/High Carbon Dioxide (+5 psi) Environment

| Time | Treatment Parameter | Hyperbaric Cycles | After Treatment | Mortality 24 h later |
|---|---|---|---|---|
| 8 h | $CO_2$ | 5 pressurized, 1 min. | 100% immobilized | 99% (198/200) |

TABLE 23

Control of Thrip Eggs (*Frankliniella occidentalis*) With a Hyperbaric Anoxic/High Carbon Dioxide (+5 psi) Environment

| Time | Treatment Parameter | Hyperbaric Cycles | After Treatment | Mortality 24 h later |
|---|---|---|---|---|
| 8 h | $CO_2$ | 5 pressurized, 1 min. | N/A | 90% (150/167) |

TABLE 24

Control of "Fruit Flies" (*Drosophila melanogaster*) in a cycled Hyperbaric/Hypobaric (−20 Hg to +2 Hg) and an Anoxic/High Carbon Dioxide and Ethanol Vapor Environment

| Time (hours) | Treatment Parameter (Hypobaric) | Effect After Treatment | Mortality 24 hrs later |
|---|---|---|---|
| 1 h | $CO_2$/10 cycles (−20 to +2 psi) | 100% Adult Mortality | 100% |
| 1 h | $CO_2$/10 cycles (−20 to +2 psi) | 100% Pupa Mortality | 100% |
| 1 h | $CO_2$/10 cycles (−20 to +2 psi) | 100% Larva Mortality | 100% |
| 1 h | $CO_2$/10 cycles (−20 to +2 psi) | 100% Egg Mortality | 100% |

TABLE 25

Control of Juvenile and Adult Mites (*Amblyseius cucumeris*) With Anoxia & Radio Frequency Secondary Effects

| Time | Treatment Parameter | Observations | After Treatment | Mortality 24 h after |
|---|---|---|---|---|
| 16 h | With $CO_2$ & 60 Hz | 3 cycles, 1 min | 99% immobilized | 99% |
| 16 h | With $CO_2$ & 60 Hz | 3 cycles, 1 min | 100% immobilized | 80% |
| 12 h | With $CO_2$ & 60 Hz | 30 cycles, 1 min | 100% immobilized | 100% |

TABLE 26

Control of Egg, Juvenile and Adult Mites (*Amblyseius cucumeris*) With The Use Of RF and Ozone

| Date | Treatment Parameter | Electrode to Commodity Distance | After Treatment | Mortality 24 h after |
|---|---|---|---|---|
| 7 h | 60 Hz, $O_3$ | 3.8-cm gap | 100% immobilized | 100% (911/911) |
| 15.5 h | 60 Hz, $O_3$ | 3.8-cm gap | 97% immobilized | 100% (1002/1002) |
| 16 h | 60 Hz, $O_3$ | 3.8-cm gap | 100% immobilized | 100% |
| 7 h | 60 Hz, $O_3$ | 3.8-cm gap | 100% immobilized | 100% |
| 16 h | 60 Hz, $O_3$ | 3.8-cm gap | 100% immobilized | 100% (1024/1024) |
| 10 h | 60 Hz, $O_3$ | 3.8-cm gap | 100% immobilized | 97.5% (390/400) |
| 16 h | 16 h, 60 Hz, $O_3$ | 3.8-cm gap | 100% immobilized | 99.5% (656/659) |
| 16 h | 16 h, 60 Hz, $O_3$ | 3.8-cm gap | 100% immobilized | 90% |
| 10 h | 10 h, 60 Hz, $O_3$ | 3.8-cm gap | 100% immobilized | 100% (1393/1393) |
| 16 h | 16 h, 60 Hz, $O_3$ | 3.8-cm gap | 100% immobilized | 100% (1646/1646) |
| 10 h | 10 h, 60 Hz, O3 | 3.8-cm gap | 100% immobilized | 99.7% (820/822) |
| 10 h | 10 h, 60 Hz, $O_3$ | 3.8-cm gap | 100% immobilized | 99.5% (1388/1395) |
| 10 h | 10 h, 60 Hz, $O_3$ | 3.8-cm gap | 100% immobilized | 99% |
| 15 h | 15 h, 60 Hz, $O_3$ | 3.8-cm gap | 100% immobilized | 100% |
| 17 h | 17 h, 60 Hz, $O_3$ | 7.5-cm gap | 97% immobilized | 93% (650/700) |
| 4 h | 4 h, 60 Hz, $O_3$ | 3.8-cm gap | 99% immobilized | 99% |
| 10 h | 10 h, 60 Hz, $O_3$ | 3.8-cm gap | 100% immobilized | 100% |

TABLE 26-continued

Control of Egg, Juvenile and Adult Mites (*Amblyseius cucumeris*) With The Use Of RF and Ozone

| Date | Treatment Parameter | Electrode to Commodity Distance | After Treatment | Mortality 24 h after |
|---|---|---|---|---|
| 16 h | 16 h, 60 Hz, $O_3$ | 3.8-cm gap | 100% immobilized | 100% |

What is claimed is:

1. A method for control of microbial organisms, comprising:

exposing a microbial organism to an environment of low oxygen and high ballast gas concentrations at a pressure below the ambient barometric pressure for a first period of time of exposure;

increasing the pressure of the environment to a level over the ambient barometric pressure but less than 20 psi for a second period of time of exposure; and cycling between a minimum pressure and a maximum pressure for a plurality of cycles.

2. A method as recited in claim 1,wherein said low oxygen environment comprises less than approximately 0.1% oxygen.

3. A method as recited in claim 1,wherein said low oxygen environment comprises less than approximately 0.01% oxygen.

4. A method as recited in claim 1,wherein said ballast gas environment comprises greater than approximately 99.9% carbon dioxide.

5. A method as recited in claim 1,wherein said low oxygen and high ballast gas environment comprises less than approximately 0.01% oxygen and greater than approximately 99.9% carbon dioxide.

6. A method for microbial control, comprising:

exposing microbes to an environment of low oxygen and high ballast gas concentrations and at least one metabolically toxic agent; and creating a pressure differential within said low oxygen-high ballast gas concentration environment, said pressure differential having a maximum pressure 20 psi or below and a minimum pressure; and cycling the pressure of said environment from said minimum pressure to said maximum pressure for a plurality of cycles.

7. A method as recited in claim 6, wherein said maximum pressure and said minimum pressure of said pressure differential are at a level that is lower than the ambient barometric pressure.

8. A method as recited in claim 6, wherein said maximum pressure and said minimum pressure of said pressure differential are at a level that is greater than the ambient barometric pressure.

9. A method as recited in claim 6, wherein said agent comprises a chemical selected from the group of chemicals consisting essentially of a nitrogen oxide, a sulfur oxide, an alcohol, an oxygen radical, ozone and hydrogen peroxide.

10. A method as recited in claim 6, wherein said toxic agent comprises a combination of a disinfectant and an antiseptic.

11. A method as recited in claim 10, wherein said disinfectant comprises hydrogen peroxide and said antiseptic comprises ethanol.

12. A method for microbial control, comprising:

evacuating substantially a chamber containing articles for treatment;

exposing microbes to an environment of low oxygen and high ballast gas concentrations at a pressure below the ambient barometric pressure for a first period of time of exposure;

exposing microbes in the low oxygen high ballast gas concentration environment to at least one metabolically toxic agent; and increasing the pressure of the environment over the ambient barometric pressure for a second period of time of exposure.

13. A method as recited in claim 12, further comprising:

creating a pressure differential within the low oxygen-high ballast gas concentration and toxic agent environment, said pressure differential having a maximum pressure and a minimum pressure; and cycling the pressure of said environment from said minimum pressure to said maximum pressure for a plurality of cycles;

wherein said maximum pressure and said minimum pressure of said pressure differential are both at a level that is greater than the ambient barometric pressure.

14. A method as recited in claim 13, wherein said pressure differential comprises:

a maximum pressure of approximately +10 pounds per square inch; and a minimum pressure of approximately +2 pounds per square inch.

15. A method as recited in claim 12, further comprising:

creating a pressure differential within the low oxygen-high ballast gas concentration and toxic agent environment, said pressure differential having a maximum pressure and a minimum pressure; and cycling the pressure of said environment from said minimum pressure to said maximum pressure for a plurality of cycles;

wherein said maximum pressure and said minimum pressure of said pressure differential are both at a level that is less than the ambient barometric pressure.

16. A method as recited in claim 15, wherein said pressure differential comprises:

a maximum pressure of approximately −2 pounds per square inch; and a minimum pressure of approximately −10 pounds per square inch.

17. A method as recited in claim 12, further comprising:

creating a pressure differential within the low oxygen-high ballast gas concentration and toxic agent environment, said pressure differential having a maximum pressure and a minimum pressure; and cycling the pressure of said environment from said minimum pressure to said maximum pressure for a plurality of cycles;

wherein said maximum pressure at a level that is greater than the ambient barometric pressure and said minimum pressure of said pressure differential is at a level that is less than the ambient barometric pressure.

18. A method as recited in claim 17, wherein said pressure differential comprises:

a maximum pressure of approximately +5 pounds per square inch; and a minimum pressure of approximately −20 pounds per square inch.

19. A method for microbial control, comprising:

evacuating rapidly a chamber containing articles for treatment;

pressurizing the evacuated chamber with a ballast gas or gases;

repeating the evacuation and ballast gas pressurization steps to produce an environment of low oxygen and high ballast gas concentrations;

exposing microbes to the environment of low oxygen and high ballast gas concentrations at a first pressure above the ambient barometric pressure for a first period of time of exposure;

decreasing the pressure of the chamber environment to a second pressure with a level below the ambient barometric pressure for a second period of time of exposure; and cycling periods of first and second pressure exposure.

20. A method as recited in claim 19, wherein said chamber is evacuated to a pressure of between −10 psi and −20 psi.

21. A method as recited in claim 19, wherein said chamber is pressurized with a ballast gas or gases to a pressure of between 0 psi and +10 psi.

22. A method as recited in claim 19, further comprising exposing microbes in the low oxygen high ballast gas concentration environment to at least one metabolically toxic agent.

* * * * *